United States Patent [19]

Morris et al.

[11] 4,238,624
[45] Dec. 9, 1980

[54] PROCESS FOR MAKING GLYCOL ESTERS

[75] Inventors: Nancy J. Morris; George D. Shier, both of Midland, Mich.

[73] Assignee: The Dow Chemical Company, Midland, Mich.

[21] Appl. No.: 90,710

[22] Filed: Nov. 2, 1979

[51] Int. Cl.$^3$ .............................................. C07C 67/05
[52] U.S. Cl. ..................................... 560/246; 252/439
[58] Field of Search ......................................... 560/246

[56] References Cited

U.S. PATENT DOCUMENTS

| 3,479,395 | 11/1969 | Huguet | 560/246 |
| 3,668,239 | 6/1972 | Kollar | 560/246 |
| 3,715,388 | 2/1973 | Valbert | 560/246 |
| 3,715,389 | 2/1973 | Hoch | 560/246 |
| 3,770,813 | 11/1973 | Kollar | 560/246 |
| 3,778,468 | 12/1973 | Kollar | 560/246 |
| 3,985,795 | 10/1976 | Kollar | 560/246 |
| 4,045,477 | 8/1977 | Sherwin | 560/246 |
| 4,087,623 | 5/1978 | Sherwin | 560/246 |

*Primary Examiner*—Natalie Trousof
*Assistant Examiner*—Michael Shippen

[57] ABSTRACT

Ethylene glycol mono- and dialkanoates are produced by the vapor phase reaction of ethylene, molecular oxygen, and a lower alkanoic acid at about 150° C.–225° C. in the presence of an iodine source and a catalyst consisting essentially of bismuth-stabilized $TeO_2$ on a carbon support.

5 Claims, No Drawings

PROCESS FOR MAKING GLYCOL ESTERS

BACKGROUND OF THE INVENTION

The present invention relates to a process for making glycol esters by a vapor phase oxidation and esterification carried out in the presence of a heterogeneous tellurium-based catalyst.

Ethylene glycol is largely produced at present by hydrolysis of ethylene oxide derived either from ethylene chlorohydrin by dehydrochlorination or from the catalytic oxidation of ethylene.

In recent years, processes have been developed whereby ethylene has been oxidized and esterified by reaction with molecular oxygen in the presence of an acetic acid solution containing a dissolved variable valence metal compound catalyst and a halogen or halide solubilizing agent or promoter, usually a bromide or chloride, at moderately elevated temperatures. Compounds of metals such as selenium, tellurium, vanadium, manganese, iron, chromium, and copper have been used as dissolved homogeneous catalysts in such liquid phase acetoxylation processes. The mono- and diacetates of ethylene glycol thereby produced are subsequently hydrolyzed by any of several known processes to produce ethylene glycol or they can be converted to vinyl acetate by pyrolysis. U.S. Pat. Nos. 3,668,239; 3,715,389; 3,770,813; and 3,985,795 are representative of those describing the oxidation-esterification or acetoxylation reaction.

The liquid phase acetoxylation processes for making glycol acetates are relatively efficient, but they have a number of serious practical disadvantages. These include the need for heavy pressure reactors, the use of expensive corrosion resistant materials because the acetic acid-halide reaction stream is highly corrosive, the necessity for handling large volumes of recycle streams, and the difficult separation of an often toxic dissolved metal catalyst from the product. There is need for an alternate approach that would avoid at least some of the more serious disadvantages.

SUMMARY OF THE INVENTION

It has now been found that many of the difficulties of the liquid phase process using a homogeneous catalyst as described above are avoided by running the oxidation-esterification reaction as a gas phase process using a particularly defined heterogeneous catalyst. This new process for making acetates or other lower alkanoates of ethylene glycol comprises reacting ethylene, molecular oxygen, and a lower alkanoic acid in the gas phase at a moderately elevated temperature in the presence of a source of iodine and a catalyst consisting essentially of a carbon support coated with about 1-20 percent by weight of $TeO_2$ and about 2-30 percent by weight of $Bi_2O_3$. The process is ordinarily run at or near atmospheric pressure although moderate superatmospheric pressure can be employed if desired. The reaction product is largely the glycol diester with a minor proportion of the monoester.

DETAILED DESCRIPTION OF THE INVENTION

The proportions of reactants and the reaction temperature are essentially those taught by prior art descriptions of the liquid phase processes using a homogeneous catalyst as set forth in the illustrative patents listed above. For example, the general temperature range for the process is about 150° C. -225° C. and the preferred temperature is about 180° C. -210° C. The proportions of reactants can vary widely, a main consideration being the selection of an ethylene:oxygen ratio which, in the presence of the other components of the feed to the reaction zone, will not form an explosive mixture. A molar ratio of about 0.1 to about 0.9 mole of oxygen per mole of ethylene usually is preferred with an alkanoic acid proportion of about 0.5 to about 2 moles, preferably about 0.5-1 mole of acid per mole of ethylene.

As to the reactants themselves, the ethylene employed can be pure or contaminated with the normally occurring inert impurities, for example, 10 percent or more of ethane or methane. Molecular oxygen is usually supplied in the form of air although other mixtures of oxygen with an inert gas containing a higher or lower concentration of oxygen can be used and pure oxygen can also be used if desired. The lower alkanoic acid can be any such acid, e.g., formic acid, acetic acid, propionic acid, or any of the isomeric butyric acids. Normally, acetic acid is preferred. The alkanoic acid is preferably the pure acid, but it can be a commercial aqueous grade, preferably containing no more than about 15 percent of water.

The iodine source can be elemental iodine, hydrogen iodide, or preferably an iodide of a lower aliphatic hydrocarbon such as methyl iodide, ethyl iodide, or ethylene diiodide. Methyl iodide is preferred. The iodine source can be present within a wide range of concentration in the reaction mixture, for example, about 0.1-20 percent by weight as iodine. Preferably this component is present in an amount to constitute (as iodine) about 0.5-5 percent of the total.

The bismuth oxide component of the catalyst has a dual role in that it activates the tellurium dioxide and also inhibits sublimation of tellurium from the solid material. Although compounds of other metals such as lithium, thallium, and particularly barium also have these effects to some extent, the bismuth oxide is necessary in order to obtain both a practical level of catalytic activity and a catalyst life of reasonable length. Bismuth oxide is preferably combined with the tellurium dioxide catalyst in at least an equal proportion by weight, for example, about one to about three times the weight of $TeO_2$. The $TeO_2$ concentration in the coated carbon catalyst is about 1-20 percent by weight, preferably about 2-8 percent. Both the tellurium and bismuth oxide components can be coated on the carbon support by any conventional means for preparing such supported catalysts. Preferably, the porous support is impregnated with a solution of appropriate concentration of a thermally decomposable metal salt, most conveniently the metal nitrate, and the dried impregnated support is roasted. A separate cycle of impregnation and roasting steps can be run for deposition of each metal oxide component.

The carbon support also appears to be necessary for a practical level of catalyst life and activity. Bismuth-stabilized tellurium catalysts supported on conventionally used materials such as alumina and silica gel were found to have little catalytic activity and short catalyst life. A relatively hard, dense carbon was found to provide the best results.

The space velocity of the gaseous feed through the bed of catalyst is not a critical factor in the operation of the process. As is usually the case in such processes, higher space velocities produce lower conversions with somewhat higher efficiency or yield of the desired esters. Space velocities in the approximate range of 100–2000 volumes per volume of catalyst per hour calculated at standard conditions are preferred and a space velocity of about 100–500 is most preferred.

Freshly prepared catalyst was found to require a period of initiation of at least about one hour during which gaseous feed mixture is passed through the catalyst bed at process temperature before the normal level of catalyst activity was reached. Color in the condensed effluent ranging from light yellow to brown served as a rough indicator of ester formation. Generally, the diester constituted about 80–90 percent of the ester fraction in the liquid product.

Catalyst Preparation

A quantity of porous carbon support was wet with a dilute nitric acid solution containing a predetermined amount of dissolved tellurium and the wet carbon was dried on a steam bath and then heated for an hour at about 150° C. The process was then repeated using a dilute nitric acid solution containing the desired proportion of a stabilizer metal compound such as $Bi(NO_3)_3$ with final drying for 1.5 hours at about 150° C. The dried support containing tellurium and stabilizer metal in the desired amounts was then loaded into the reactor for testing.

Reactor and Procedure

The granular coated carbon was loaded into a 51 cm × 1.25 cm electrically heated vertical glass tube reactor having an axial glass thermocouple well to form a 10 ml catalyst bed approximately in the middle of the reactor. The bed was supported by granular silicon carbide and was covered by another layer of silicon carbide. The liquid feed, acetic acid containing dissolved iodine source, was fed at a measured rate by a syringe pump into the top of the reactor and the gaseous reactants, ethylene and air or other nitrogen-oxygen mixture, were metered into the top of the reactor by calibrated rotameters.

The reactor was first heated to the desired reaction temperature and purged with nitrogen. The ethylene flow was then started and continued for several minutes before starting the oxygen-nitrogen mixture to prevent formation of explosive mixtures of ethylene and oxygen. Metered amounts of liquid reactants were then admitted to the catalyst bed. Liquid products and effluent gas were collected from the bottom of the reactor tube after about one hour or more of running time and were analyzed chromatographically.

EXAMPLES 1–4

Examples 1–3 summarized in Table 1 were made using a 10 ml catalyst bed of 4 percent $TeO_2$ and 8 percent $Bi_2O_3$ on Armak carbon beads (petroleum-derived carbon produced by Armak Industrial Chemicals Division, Chicago) with an ethylene flow of 12 ml/min, air flow 18 ml/min, and 1.0–1.8 ml/hr of acetic acid containing 1 mole percent of dissolved $CH_3I$. Example 4 was run in the same way except for using 15 ml/min $N_2$ + 20 ml/min $O_2$ instead of air. Catalyst bed temperature was held at 185° C. –195° C.

TABLE 1

| Example No. | Feed Rate, ml/hr. acetic acid + $CH_3I$ | Time min. | % Conv. $C_2H_4$ | % Selectivity EGA[1] |
|---|---|---|---|---|
| 1 | 1.0 | 148 | 12.2 | 41.5 |
| 2 | 1.72 | 60 | 22.5 | 33.0 |
| 3 | 1.8 | 80 | 24.8 | 22.5 |
| 4 | 1.8 | 118 | 24.0 | 7.4 |

[1] Mono- and diacetates of ethylene glycol.

EXAMPLES 5–12

Experiments using the apparatus and procedure of Examples 1–4 were carried out using bismuth-stabilized tellurium catalysts coated on other carbon supports. These experiments were run using methyl iodide (1 mole percent in acetic acid as in Examples 1–4) as promoter in all cases but one and effluent products were analyzed after running from one to 2.5 hours. The results are listed in Table 2.

TABLE 2

| Example No. | Catalyst Composition | Feed, ml/min $C_2H_4$ | Air | ml/hr HOAc + $CH_3I$ | Temp. °C. | Wt. % Composition of Products[1] | | | |
|---|---|---|---|---|---|---|---|---|---|
| | | | | | | $H_2O$ | HOAc | EGMA[2] | EGDA[2] |
| 5 | 2% $TeO_2$ + 4% $Bi_2O_3$ on coconut carbon | 20 | 30 | 1.72 | 190 | 9.3 | 72.8 | 2.34 | 10.9 |
| 6 | 2% $TeO_2$ + 4% $Bi_2O_3$ on coconut carbon | 20 | 30 | 1.0 | 190 | 11.0 | 73.1 | 1.7 | 9.6 |
| 7 | 2% $TeO_2$ + 4% $Bi_2O_3$ on coconut carbon | 20 | 30 | 0.7 | 180 | 12.5 | 62.6 | 3.45 | 13.7 |
| 8 | 2% $TeO_2$ + 4% $Bi_2O_3$ on coconut carbon | 25 | 40 | 1.72 | 180 | 10.8 | 57.5 | 2.11 | 20.8 |
| 9 | 4% $TeO_2$ + 8% $Bi_2O_3$ on Saran carbon[3] | 20 | 30 | 1.72 | 185 | 11.9 | 73.9 | 1.17 | 5.8 |
| 10 | 4% $TeO_2$ + 8% $Bi_2O_3$ on Saran carbon[3] | 20 | 30 | 1.72 | 195 | 9.2 | 64.1 | 1.81 | 17.2 |
| 11 | 4% $TeO_2$ + 8% $Bi_2O_3$ on Saran carbon[3] | 25 | 40 | 3.43 | 185 | 6.5 | 51.3 | 1.76 | 17.0 |
| 12 | 4% $TeO_2$ + 8% $Bi_2O_3$ on Saran carbon[3] | 25 | 40 | 3.43[4] | 180 | 4.8 | 74.3 | 2.01 | 14.6 |

[1] Wt. % Composition of Product = amount of component present based on a gas chromatographic internal standard method.
[2] EGMA and EGDA refer respectively to the monoacetate and diacetate of ethylene glycol.
[3] Carbon made from the pyrolytic dehydrochlorination of vinylidene chloride polymers, see U.S. Pat. No. 3,967,928.
[4] Promoter was $I_2$, 0.5 mole percent in acetic acid.

We claim:

1. In a process for reacting a mixture of ethylene, molecular oxygen, and lower alkanoic acid at a moderately elevated temperature in the presence of a halogen-containing promoter and a tellurium catalyst to produce a mixture of the monoalkanoate and the dialkanoate of ethylene glycol, the improvement wherein the mixture is reacted in the gas phase in the presence of a source of iodine and a heterogeneous catalyst consisting essentially of carbon coated with about 1–20 percent of $TeO_2$ and about 2–30 percent of $Bi_2O_3$ based on the weight of the coated carbon catalyst.

2. The process of claim 1 wherein the lower alkanoic acid is acetic acid.

3. The process of claim 2 wherein the source of iodine is methyl iodide.

4. The process of claim 2 wherein the catalyst contains about 2–8 percent by weight of $TeO_2$ and the $Bi_2O_3$ content is about 1–3 times the content of $TeO_2$.

5. The process of claim 2 wherein the temperature is about 150° C.–225° C.